(12) United States Patent
Chew et al.

(10) Patent No.: US 7,153,957 B2
(45) Date of Patent: Dec. 26, 2006

(54) REGIOSELECTIVE SYNTHESIS OF CCI-779

(75) Inventors: Warren Chew, Outremont (CA); Chia-Cheng Shaw, St. Laurent (CA)

(73) Assignee: Wyeth, Madison, NJ (US)

( * ) Notice: Subject to any disclaimer, the term of this patent is extended or adjusted under 35 U.S.C. 154(b) by 207 days.

(21) Appl. No.: 10/903,062

(22) Filed: Jul. 30, 2004

(65) Prior Publication Data

US 2005/0033046 A1   Feb. 10, 2005

Related U.S. Application Data

(60) Provisional application No. 60/493,249, filed on Aug. 7, 2003.

(51) Int. Cl.
*C07D 498/22* (2006.01)
*C07D 5/02* (2006.01)

(52) U.S. Cl. ...................................... 540/456; 549/213
(58) Field of Classification Search ................. 540/456; 549/213
See application file for complete search history.

(56) References Cited

U.S. PATENT DOCUMENTS 5,362,718 A   11/1994   Skotnicki et al.

6,197,967 B1   3/2001   Vollmueller et al.
6,277,983 B1   8/2001   Shaw et al.

FOREIGN PATENT DOCUMENTS

WO   WO 95/28406 A1   10/1995

OTHER PUBLICATIONS

Steffan et al, Base Catalyzed Degradations of Rapamycin, Tetrahedron Letters, vol. 34, No. 23, pp. 3699-2702, (1993).
Skotnicki et al, Synthesis of Secorapamycin Esters and Amides[1], Tetrahedron Letters, vol. 35, No. 2, pp. 197-200, (1994).
Sehgal, Sirolimus: A New Immunosuppressive Agent, Chapter 12.1, Principles of Drug Development in Transplantation and Autoimmunity, pp. 271-282, (1996).
Caufield et al, Structure-Activity Involving Modifications to the Macrolides FK-506 and Rapamycin, Current Pharmaceutical Design, vol. 1, No. 2, pp. 145-160, (1995).
Sehgal et al, Rapamycin: A Novel Immunosuppressive Macrolide, Medicinal Research Reviews, vol. 14, No. 1, pp. 1-22, (Jan. 1994).
Hughes et al, The Isolation, Synthesis and Characterization of An Isomeric Form of Rapamycin, Tetrahedron Letters, vol. 33, No. 33, pp. 4739-4742, (1992).
H. Piotrowska, et al., Heterocyclic Derivatives of Ethyl Nitroacetate, Bulletin De L'Academie Polonaise Des Sciences, May 26, 1971, pp. 591-594, vol 19, No. 10, XP009043676.

*Primary Examiner*—Bruck Kifle
(74) *Attorney, Agent, or Firm*—Howson & Howson LLP; Arnold S. Milowsky

(57) ABSTRACT

A method for regioselective synthesis of CCl-779 based on boronate chemistry is provided. Also provided are novel intermediates useful in this method.

49 Claims, No Drawings

REGIOSELECTIVE SYNTHESIS OF CCI-779

CROSS-REFERENCE TO RELATED APPLICATIONS

This application claims the benefit under 35 USC 119(e) of U.S. patent application Ser. No. 60/493,249, filed Aug. 7, 2003.

BACKGROUND OF THE INVENTION

This invention provides a regioselective synthesis of CCl-779, which is useful as an antineoplastic agent.

Rapamycin 42-ester with 3-hydroxy-2-(hydroxymethyl)-2-methylpropionic acid (CCl-779) is an ester of rapamycin which has demonstrated significant inhibitory effects on tumor growth in both in vitro and in vivo models.

CCl-779 may delay the time to progression of tumors or time to tumor recurrence which is more typical of cytostatic rather than cytotoxic agents. CCl-779 is considered to have a mechanism of action that is similar to that of sirolimus. CCl-779 binds to and forms a complex with the cytoplasmic protein FKBP, which inhibits an enzyme, mTOR (mammalian target of rapamycin, also known as FKBP12-rapamycin associated protein [FRAP]). Inhibition of mTOR's kinase activity inhibits a variety of signal transduction pathways, including cytokine-stimulated cell proliferation, translation of mRNAs for several key proteins that regulate the G1 phase of the cell cycle, and IL-2-induced transcription, leading to inhibition of progression of the cell cycle from G1 to S. The mechanism of action of CCl-779 that results in the G1-S phase block is novel for an anticancer drug.

In vitro, CCl-779 has been shown to inhibit the growth of a number of histologically diverse tumor cells. Central nervous system (CNS) cancer, leukemia (T-cell), breast cancer, prostate cancer, and melanoma lines were among the most sensitive to CCl-779. The compound arrested cells in the G1 phase of the cell cycle.

In vivo studies in nude mice have demonstrated that CCl-779 has activity against human tumor xenografts of diverse histological types. Gliomas were particularly sensitive to CCl-779 and the compound was active in an orthotopic glioma model in nude mice. Growth factor (platelet-derived)-induced stimulation of a human glioblastoma cell line in vitro was markedly suppressed by CCl-779. The growth of several human pancreatic tumors in nude mice as well as one of two breast cancer lines studied in vivo also was inhibited by CCl-779.

The preparation and use of hydroxyesters of rapamycin, including CCl-779, are disclosed in U.S. Pat. No. 5,362,718. A regiospecific synthesis of CCl-779 is described in U.S. Pat. No. 6,277,983.

CCl-779 can be synthesized by the non-regioselective acylation of rapamycin, as described in U.S. Pat. No. 5,362,718. The synthesis, however, is complicated by mixtures of the desired 42-ester, with 31-esterified rapamycin, as well as 31, 42-diesterified rapamycin and unreacted rapamycin.

CCl-779 can also be prepared by the acylation of the 31-silyl ether of rapamycin with a ketal of bis-(hydroxymethyl)propionic acid, followed by removal of the 31-silyl ether and ketal protecting group from the bis-(hydroxymethyl) propionic acid, as described in U.S. Pat. No. 6,277,983. However, the crude 42-monoester produced from this regioselective synthesis requires further purification by column chromatography to remove residual amounts of diester by-products and unreacted rapamycin starting material.

SUMMARY OF THE INVENTION

This invention provides a regioselective synthesis of rapamycin 42-ester with 3-hydroxy-2-(hydroxymethyl)-2-methylpropionic acid (CCl-779) based on boronic acid chemistry. This invention overcomes the complexity and often-laborious purification of the rapamycin 42-monoester obtained using prior methods.

Other aspects and advantages of the present invention will be readily apparent from the followed detailed description of the invention.

DETAILED DESCRIPTION OF THE INVENTION

The present invention provides a regioselective synthesis of a 42-ester of rapamycin by acylating a rapamycin 31-silyl ether with a compound of formula

$$HOOC.CR^7R^8R^9$$

or a mixed anhydride thereof, wherein:

$R^7$ is hydrogen, alkyl of 1–6 carbon atoms, alkenyl of 2–7 carbon atoms, alkynyl of 2–7 carbon atoms, $-(CR^{12}R^{13})_fOR^{10}$, $-CF_3$, $-F$, or $-CO_2R^{10}$;

$R^{10}$ is hydrogen, alkyl of 1–6 carbon atoms, alkenyl of 2–7 carbon atoms, alkynyl of 2–7 carbon atoms, triphenylmethyl, benzyl, alkoxymethyl of 2–7 carbon atoms, chloroethyl, or tetrahydropyranyl;

$R^8$ and $R^9$ are taken together to form X;

X is 2-phenyl-1,3,2-dioxaborinan-5-yl or 2-phenyl-1,3,2-dioxaborinan-4-yl, wherein the phenyl may be optionally substituted;

$R^{12}$ and $R^{13}$ are each, independently, hydrogen, alkyl of 1–6 carbon atoms, alkenyl of 2–7 carbon atoms, alkynyl of 2–7 carbon atoms, trifluoromethyl, or $-F$; and $f=0$–6; to give a 42-ester boronate 31-silyl ether of rapamycin.

Thereafter, the rapamycin 31-silyl ether, 42-boronate is hydrolyzed under mildly acidic conditions to form a rapamycin 42-ester boronate. The rapamycin 42-ester boronate is treated with a suitable diol. The process permits preparation of a regiospecific rapamycin 42-ester.

The preparation, isolation and purification of a rapamycin 42-ester from a rapamycin silyl ether according to the method of the invention entails a trans-boronation reaction in which the phenylboronate piece from the compound is transferred to a diol. A precipitation of the rapamycin 42-ester from ether:heptanes follows this trans-boronation. The synthetic route of this invention offers several distinct advantages over the synthetic methodology previously published for the preparation of rapamycin esters or ethers; mainly in the purification, reduction in cost of goods, increased safety, increased throughput and plant time reduction. This method of the invention provides a new approach to the manufacture of rapamycin 42-esters (e.g., CCl-779). A laborious chromatographic step previously used in all large scale batches of the illustrated CCl-779 has been eliminated. The large amount of solvent required in the chromatography described in U.S. Pat. No. 6,277,983 has been eliminated thereby reducing cost of goods. The plant reactor time and resources are reduced by 50%. The size of the reactor needed for large-scale synthesis of CCl-779 is reduced thereby increasing the overall throughput. The novel trans-boronation procedure described in this invention reduces overall processing time. The final diethyl ether purification in previous synthesis methods has also been eliminated with a built-in purification procedure in this invention.

According to the invention, a 31-silyl ether rapamycin is acylated using a compound of formula HOOC.CR$^7$R$^8$R$^9$ or anhydride thereof, as defined above to provide a 31-silylethyl, 42-ester boronate. In one embodiment, a rapamycin 31-silyl ether is acylated using a 5-methyl-2-boronate[1,3-dioxane]-5-carboxylic acid (exemplified by compound [A] in Scheme 1 below) or a 2,4,6-trichlorobenzoyl mixed anhydride of 5-methyl-2-phenyl-1,3,2-dioxoborinane-5-carboxylic acid.

One particularly desirable method for the preparation of rapamycin 31-silyl ethers is provided in U.S. Pat. No. 6,277,983. The invention is not limited to this method of obtaining rapamycin 31-silyl ethers. However, it is currently preferred that the 31-silyl ether of rapamycin is rapamycin 31-O-trimethylsilyl ether.

In one embodiment, a rapamycin 31-silyl ether is characterized by having the formula:

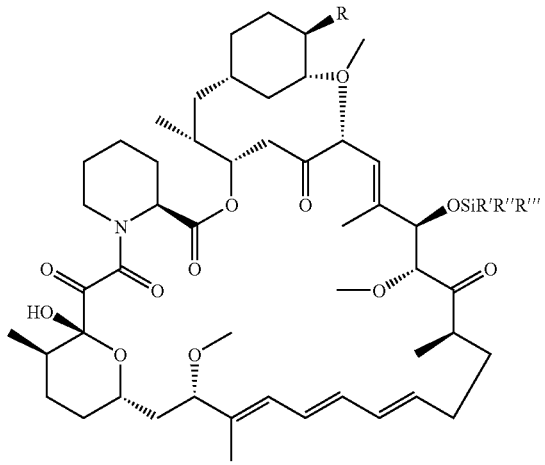

where R is selected from:

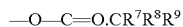

wherein:

R$^7$ is hydrogen, alkyl of 1–6 carbon atoms, alkenyl of 2–7 carbon atoms, alkynyl of 2–7 carbon atoms, —(CR$^{12}$R$^{13}$)$_f$OR$^{10}$, —CF$_3$, —F, or —CO$_2$R$^{10}$;

R$^{10}$ is hydrogen, alkyl of 1–6 carbon atoms, alkenyl of 2–7 carbon atoms, alkynyl of 2–7 carbon atoms, triphenylmethyl, benzyl, alkoxymethyl of 2–7 carbon atoms, chloroethyl, or tetrahydropyranyl;

R$^8$ and R$^9$ are taken together to form X;

X is 2-phenyl-1,3,2-dioxaborinan-5-yl or 2-phenyl-1,3,2-dioxaborinan-4-yl, wherein the phenyl may be optionally substituted;

R$^{12}$ and R$^{13}$ are each, independently, hydrogen, alkyl of 1–6 carbon atoms, alkenyl of 2–7 carbon atoms, alkynyl of 2–7 carbon atoms, trifluoromethyl, or —F; and f=0–6;

and wherein R', R", and R''' are the same or different and are selected from alkyl of 1–6 carbon atoms, phenyl and benzyl.

The present invention provides compound [A] as a novel compound useful for production of CCl-779 and analogues thereof. The preparation of compound [A] involves mixing a phenylboronic acid with 2,2-bis(hydroxymethyl)-propionic acid at room temperature to give a phenylborinane. Typical yields are >90%. The reaction can be conducted in methylene chloride but the preferred solvent is tetrahydrofuran (THF).

Desirably, the phenylborinane is a 2-phenyl-1,3,2-dioxoborinane-5-carboxylic acid wherein the phenyl is optionally substituted. In another embodiment, the phenylborinane is a 2-phenyl-1,3,2-dioxaborinan-4-yl, wherein the phenyl is optionally substituted. One particularly desirable substitution on the phenyl group is an alkyl, most desirably a $C_1$, $C_2$, $C_3$, $C_4$, $C_5$, or $C_6$ alkyl. Other aryl- (including phenyl-) boronic acids can be used in this reaction. These include mono, di and tri-substituted arylboronic acids in which the substituents are the same or different. Substituents on the aryl group include halogen, alkyl, alkoxy, aryloxy (e.g., phenoxy), aralkyl, nitro, cyano, fused phenyl such has naphthalylboronic acid. The term alkyl when used as a group or part of a group such as alkoxy or aralkyl includes-alkyl moieties of 1 to 12 carbon atoms, e.g., 1–6 carbon atoms. The term aryl as a group or part of a group, e.g., aralkyl or aryloxy means an aromatic group including those of 6–10 carbon atoms, such as phenyl or naphthyl. The preferred arylboronic acid is phenylboronic acid.

Briefly, it is preferred that rapamycin is bis-silylated at the 31 and 42 positions with trimethylsilyl chloride followed by regioselective de-silylation at the 42-position with dilute sulfuric acid. The isolated product is acylated at the 42-position with the anhydride derived from the 2-phenylboronate acid. Dimethylaminopyridine was added as the catalyst to drive the reaction to completion. The reaction required ~3 equivalents of mixed anhydride to consume all of the 31-trimethylsilyl rapamycin. After workup of the reaction, the resulting solution was stored at 0 to 10° C. until needed in the next step. On standing in acetone solution, the product will undergo disassociation to compound [B]. This does not present an issue, as the next step is hydrolysis of the silyl functional group. Almost complete conversion (<3%) to [B] was achieved after 83 days in acetone at 0 to 10° C.

The formation of the mixed anhydride can be followed by REACTIR (ASI Applied Systems). The REACTIR (ASI Applied Systems) system is a specially designed instrument for real-time, in-situ analysis of a variety of chemical reactions. Given that the mixed anhydride is formed from a carboxylic acid and an acid chloride, the reaction is well suited for monitoring by infrared spectroscopy (IR). IR is a powerful method for detecting the presence of carbonyl functional groups, and in the case of REACTIR, for monitoring the appearance or disappearance of carbonyl functional groups. In a typical REACTIR (ASI Applied Systems) process, compound [A] was mixed with diisopropylethylamine in methylene chloride and cooled to 0–5° C. in an ice bath. An IR spectrum was taken that serves as a background scan. 2,4,6-Trichlorobenzoyl chloride was then added. A second IR spectral scan was taken which serves as the T=0 min (i.e., the start of the reaction). The experiment was setup to acquire an IR spectrum every 5 mins for 5 hr maintaining the bath temperature at 0 to 5° C. The key characteristic bands were 1818 cm$^{-1}$, 1741 cm$^{-1}$ and 1031 cm$^{-1}$. When the acid chloride was added to the mixture of compound [A] and diisopropylethylamine (T=0 min), the spectrum showed essentially no peak signal. However, the carbonyl and anhydride (C—O—C) frequency regions had increased with time indicative of formation of the mixed anhydride.

The mixed anhydride reaction can be conducted in ethyl acetate, t-butyl methyl ether, diethyl ether, and tetrahydrofuran (THF) butyl the reactions are more sluggish. The preferred solvent is methylene chloride for its ease of reaction completion. DMAP is the preferred base catalyst for this reaction. Other bases that can be used is 4-pyrrolidinopyridine, N-methyl imidazole and pyridine.

The mixed anhydride is an unstable species and is prepared in situ at low temperatures. It is stable for up to 48 hr at −5 to 0° C. It can be prepared from −50 to 20° C. but the preferred temperature range is −6 to 5° C. The mixed anhydride is aged for up to 8 hr before the coupling reaction.

The preferred holding time is 4 to 5 hr prior to addition of the 31-trimethylsilyl (TMS) rapamycin coupling partner.

The coupling reaction may be conducted from −20° C. to 20° C. but the preferred temperature range is −11° C. to −5° C. At higher temperatures, the reaction becomes more sluggish and additional charges of mixed anhydride were needed for completion. At lower temperatures, the mixed anhydride is more stable albeit the reaction time is longer. The reaction is generally completed within 12 to 17 hr.

Compound [B] was prepared, isolated and purified in a 3-step 1-reaction container sequence. The key element in this reaction was the choice of acetone as the solvent. Other solvents that can be used in this preparation include diethyl ether, acetonitrile, ethyl acetate, THF, t-butyl methyl ether and methylene chloride. Currently, acetone is the preferred solvent.

Thus, 31-trimethylsilyl CCl-779 boronate, [D], is dissolved in acetone as a concentrate. However, in certain embodiments, hydrolysis can be performed using a single phase aqueous acid/organic solvent system.

Hydrolysis of the 31-trimethylsilyl group (to provide [B]) is performed under mildly acidic conditions. Thus, the selected organic solvent (e.g., acetone) is mixed with a dilute inorganic acid such as, e.g., sulphuric, hydrochloric or phosphoric acid. Examples of suitable dilute inorganic acid concentrations range from about 0.1 N to about 3N, about 0.2 N to about 2N, or about 0.5 N. Typically, this step is carried out at a temperature of about 25° C. or below, from about −5° C. to about 10° C., or about 0° C. to about 5° C. Desirably, this step is carried out at a pH of 5 to 6. Optionally, a suitable buffer, e.g., sodium acetate, or in the presence of sodium bicarbonate and/or acetic acid are added to the mixture to adjust or maintain the pH in the desired range.

In the examples below, the hydrolysis reaction uses 0.5 N sulfuric acid at 0 to 5° C. The reaction is typically complete in 5 to 6 hours and compound [B] was easily obtained by a simple filtration. However, the use of fluoride based reagents to remove the 31-trimethylsilyl group is not preferred as decomposition products are formed.

The rapamycin 42-boronate ester is a novel intermediate useful in the method of the invention for preparation of a rapamycin 42-ester. In one embodiment, the intermediate is rapamycin 42-ester with 5-methyl-2-phenyl-1,3,2-dioxaborinate-5-carboxylic acid.

In one embodiment, the invention provides a rapamycin 42-ester boronate compound of formula I:

(I)

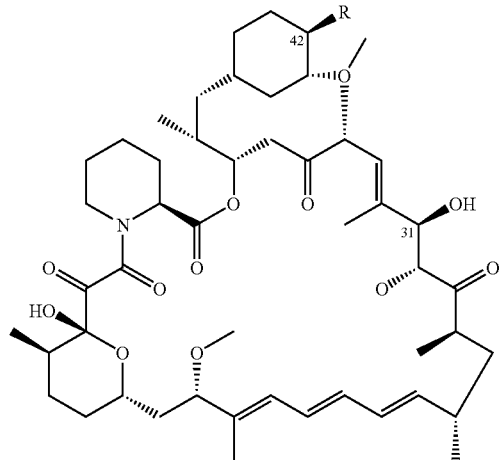

wherein R is selected from:

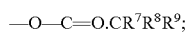

—O—C═O.CR⁷R⁸R⁹;

wherein $R^7$ is hydrogen, alkyl of 1–6 carbon atoms, alkenyl of 2–7 carbon atoms, alkynyl of 2–7 carbon atoms, —$(CR^{12}R^{13})_f$ $OR^{10}$, —$CF_3$, —F, or —$CO_2R^{10}$;

$R^{10}$ is hydrogen, alkyl of 1–6 carbon atoms, alkenyl of 2–7 carbon atoms, alkynyl of 2–7 carbon atoms, triphenylmethyl, benzyl, alkoxymethyl of 2–7 carbon atoms, chloroethyl, or tetrahydropyranyl;

$R^8$ and $R^9$ are taken together to form X;

X is 2-phenyl-1,3,2-dioxaborinan-5-yl or 2-phenyl-1,3,2-dioxaborinan-4-yl, wherein the phenyl may be optionally substituted;

$R^{12}$ and $R^{13}$ are each, independently, hydrogen, alkyl of 1–6 carbon atoms, alkenyl of 2–7 carbon atoms, alkynyl of 2–7 carbon atoms, trifluoromethyl, or —F; and f=0–6.

At this stage in the method of the invention, the rapamycin 42-ester boronate prepared according to the method of the invention usually is present as B and C isomers of the compound. [These two isomers of exemplary compound [B] are illustrated below.] At this stage, the B:C isomer ratio is normally <10:1. The inventors have found that the B isomer is more crystalline than the C isomer and is less soluble in acetone than the C isomer. In order to take advantage of these properties, the inventors have shown that in sodium acetate buffer at a pH 5 to 6, the B:C isomer ratio can be increased to above 20:1. By increasing this ratio, recovery of compound [B] can be increased. Thus, it is desirable to raise the B:C isomer ratio to at least 1:1, more desirably, above 5:1, above 10:1, above 15:1, above 20:1, and most preferably to about 25:1. Sodium bicarbonate was added to neutralize sulfuric acid and adjust the pH to 7 to 8. Acetic acid was then added to form sodium acetate and to drop to pH 5 to 6. After holding the reaction mixture for 16 h, the isomer ratio becomes ~25:1. Other buffers can be used such as potassium acetate and zinc acetate but the preferred one is sodium acetate.

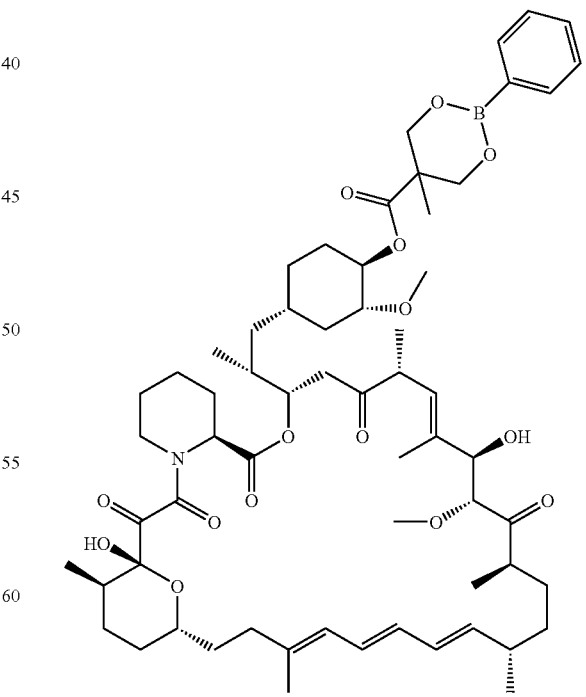

[B] B isomer

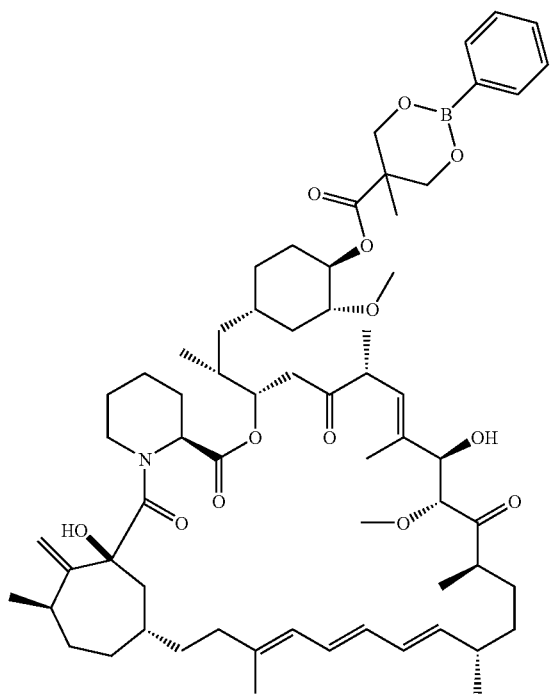

[B] C isomer

The mixture was filtered, washed and dried to provide crude compound [B]. The mother liquors contain-predominantly the C isomer, the bis-ester byproducts and other unknown impurities related to the crystal crude rapamycin starting material.

To facilitate obtaining clean product, it is essential at this point to monitor the rapamycin level in the crude compound [B]. The rapamycin content is typically ~5% (area %) by high performance liquid chromatograph (HPLC). Recrystallizations lower the rapamycin content to <0.7%. Purification in suitable solvents such as acetone could reduce rapamycin levels. Compound [B], as illustrated in the scheme, is a solid white powder that is stable at room temperature.

The reaction can be conducted in a solvent such as an ether solvent, or preferably, THF, diluting the reaction mixture with t-butyl methyl ether or toluene and applying an aqueous extraction method to remove excess diol and diol-boronate by-products. Both diol and diol-boronate are water-soluble. The preferred method eliminated aqueous extraction. The preferred method involves a simple filtration step. The process involves dissolving compound [B] in THF, t-butyl methyl ether or acetonitrile, adding the diol and mixing at room temperature for 3 h. The solvent was distilled to provide the reaction mixture as a foam/oil. Ether was added and the product was co-precipitated with heptanes. The process can be repeated to produce CCl-779 in 80% to 90% yield from compound [B].

The initial treatment with diol removes the majority of the phenylboronic acid in the reaction mixture. Residual amounts of phenylboronic acid still remaining are readily scavenged by an additional treatment with diol. The final compound [C] resulting from this practice show that phenylboronic acid content is acceptable. Excess diol in the transboronation treatment can be used but the preferred amount is 1 to 5 mole equivalents. The yield obtained from this trans-boronation was 86%. The overall yield from rapamycin was 47% to 50%.

A variety of 1,2-, 1,3-, 1,4- and 1,5-diols can be used to effect this transboronation. Alkyl substituted diols are preferable such as 2-methyl-2,4-pentanediol. Diethanolamine or solid-supported polystyrene diethanolamine (PS-DEAM) were useful. Transboronation can also be achieved using carboxylic acid reagents such as oxalic, malonic, tartaric, phthalic and salicylic acid. 2,2-Bis(hydroxymethyl)propionic acid was effective but could not be removed from the final product.

The process is exemplified in the following scheme. This scheme is illustrative only, and does not limit the invention.

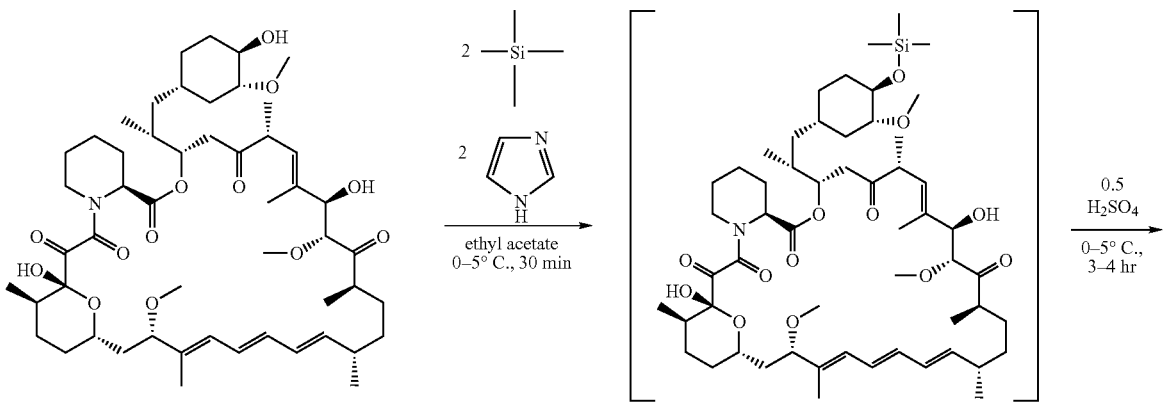

Rapamycin

-continued
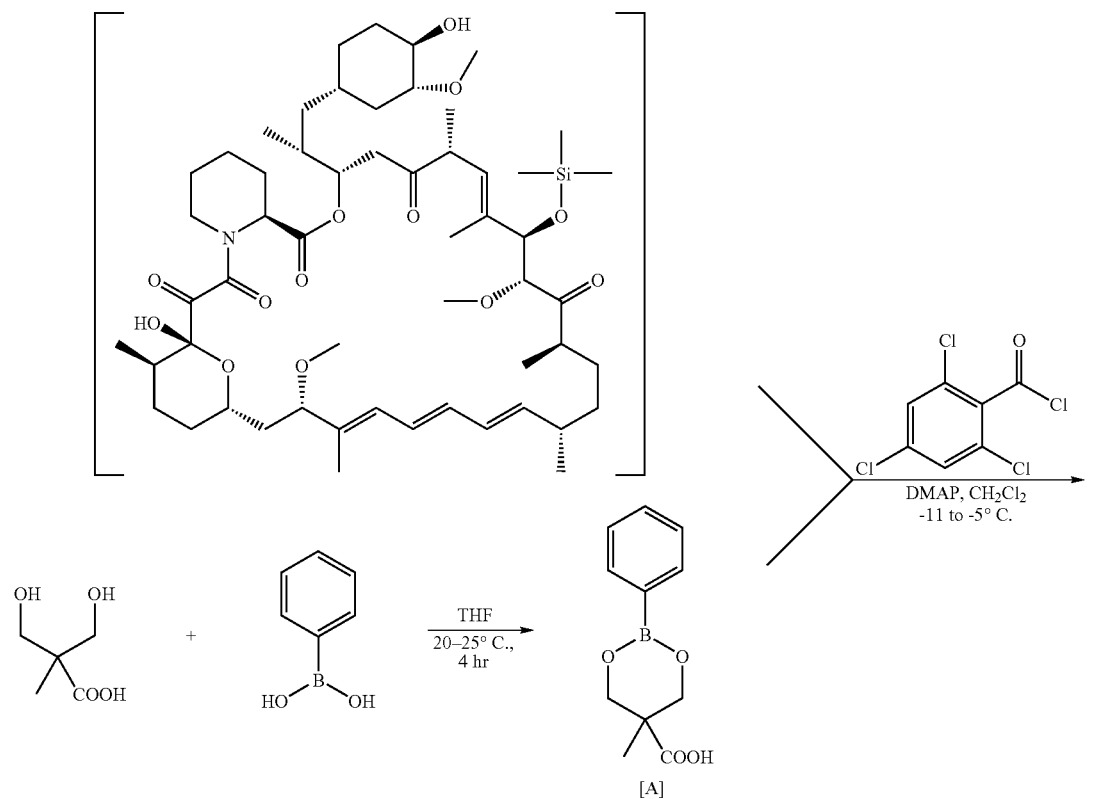
[A]
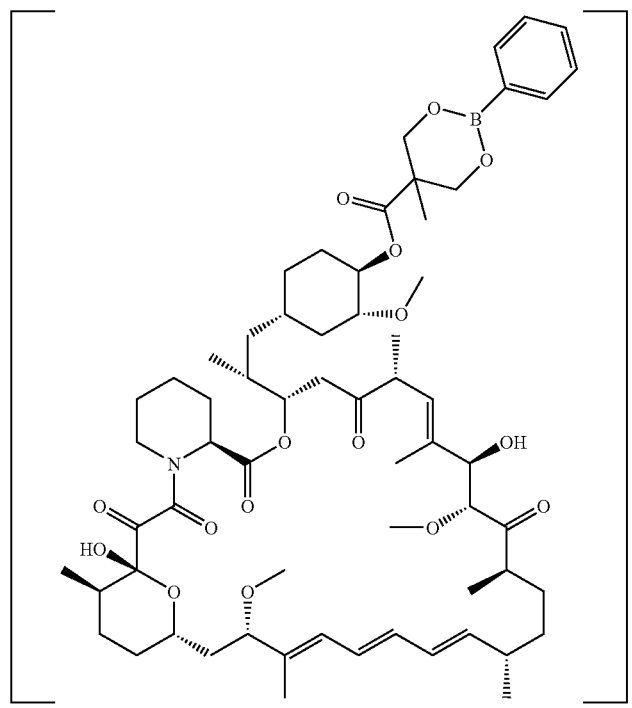
[D]

-continued
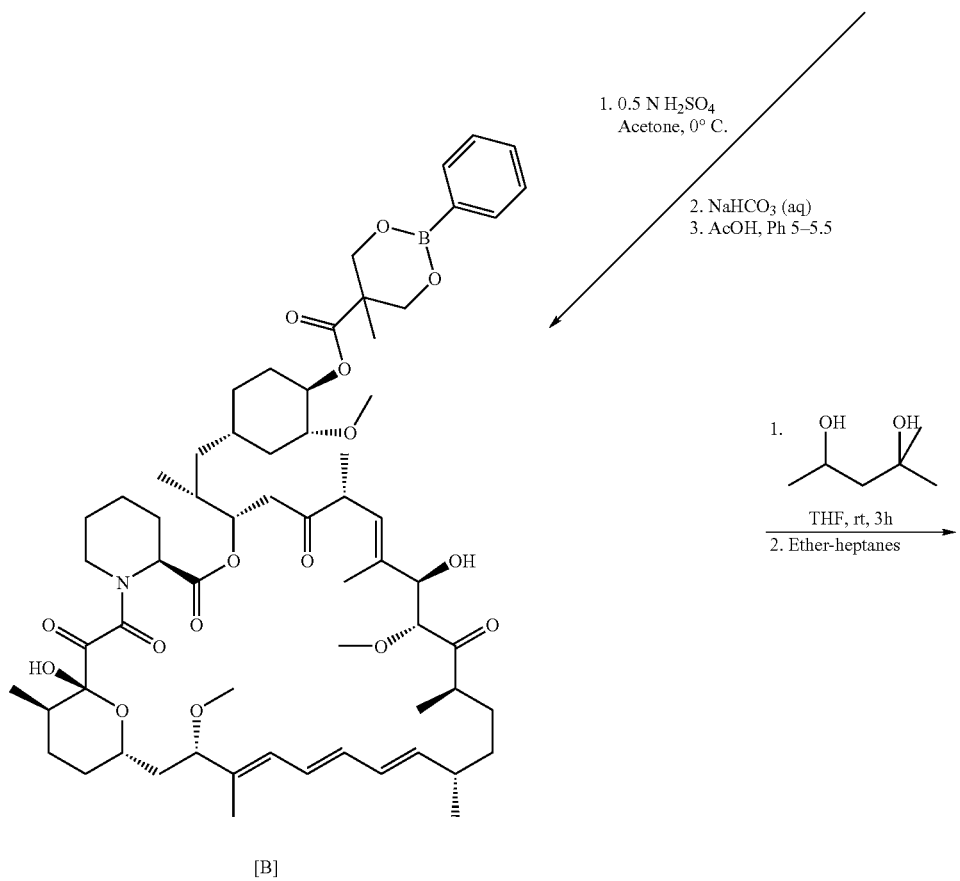
[B]
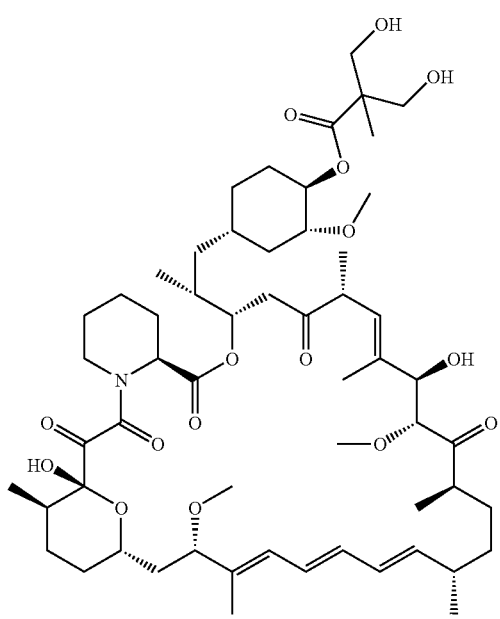
[C]
CCI-779

Preparation of 5-Methyl-2-phenyl-1,3,2-dioxaborinane-5-carboxylic acid, [A]

To a suspension of 2,2-bis(hydroxymethyl)propionic acid (131 g, 0.98 mole) in tetrahydrofuran (500 ml) was added a solution of phenylboronic acid (122 g, 1.0 mole) in tetrahydrofuran (500 ml). The mixture was stirred for 3 h and toluene (1.0 L) was added. Water was removed by azeotropic distillation with toluene. Heptanes (500 ml) was added to the precipitated product, heated to reflux and cooled. The mixture was filtered and washed with heptanes (2×300 ml). The solids were dried under vacuum at 70–75° C. until constant weight to give 94% yield. $^1$H NMR: δ (DMSO-d6) 7.65 (d, 2H, Ar), 7.40 (m, 3H, Ar), 4.35 (d, 2H, $CH_2$), 3.92 (d, 2H, $CH_2$), 1.17 (s, 3H, $CH_3$)

Preparation of Rapamycin 42-ester with 5-methyl-2-phenyl-1,3,2-dioxaborinane-5-carboxylic acid, [B]

As described in U.S. Pat. No. 6,277,983 (2001) a 3 L flask was charged with rapamycin (100 g, 0.104 mole) and dissolved in ethyl acetate (1.50 L). The solution was cooled to 5–10° C. Imidazole (30 g, 0.44 moles, 4.23 eq.) was added and dissolved. Under nitrogen protection, trimethylsilyl chloride (44 g, 0.405 mole, 4.0 eq.) was added over 30–40 min while maintaining the temperature at 0–5° C. during the addition. The mixture was held for a minimum of 0.5 h. The reaction was monitored by TLC (30:70 acetone:heptane eluent). The reaction was complete when all of the rapamycin was consumed.

Two to three drops of the reaction mixture were removed and retained as a 31,42-bis(trimethylsilyl) rapamycin reference standard. 0.5 N Sulfuric acid (300 mL) was added to the 3 L flask over 0.5 h maintaining the temperature 0–5° C. The mixture was stirred vigorously and held for 5 h. The reaction was monitored by thin layer chromatography (TLC) (30:70 acetone:heptane eluent). The reaction was complete when essentially no 31,42-bis-(trimethylsilyl) rapamycin was present. The layers were separated and the lower aqueous layer was back extracted with ethyl acetate (500 mL). The combined organic layers were washed with saturated brine (500 mL) and saturated sodium bicarbonate (2×200 mL) until pH 8 was obtained. The organic layer was washed with water (2×500 mL) and brine (500 ml) until pH 6 to 7 was obtained. The solution was dried over magnesium sulfate (100 g) for 30 min, filtered into a 2 L flask and concentrated to a volume of 135 ml. Ethyl acetate (500 ml) was added and concentrated to a volume of 135 ml. The water chase was repeated once more with ethyl acetate (500 ml). Methylene chloride (300 ml) was added and the solution held until needed in the next step.

A 3 L flask equipped with mechanical stirrer was charged with compound [A] (75 g, 0.341 mole) in methylene chloride (400 mL). Diisopropylethylamine (66.1 g, 0.51 mole) was added dropwise over 20 mins and rinsed with methylene chloride (25 mL). 2,4,6-Trichlorobenzoyl chloride (80 g, 0.328 mole) was added and rinsed with methylene chloride (25 mL). The mixture was held at 0–5° C. for 4 h, and cooled to −10±5° C.

The solution of 31-trimethylsilyl rapamycin was added to the 3 L flask containing the mixed anhydride, and rinsed with methylene chloride (25 mL). A solution of dimethylamino pyridine (48.5 g, 0.397 mole) in methylene chloride (150 mL) was prepared, added over 1.5 h, maintaining the temperature <−8° C., and rinsed with methylene chloride (25 mL). The mixture was held for 12 h at −11 to −5° C. The reaction mixture was quenched with 1 N sulfuric acid (600 ml) keeping the temperature <10° C. The mixture was stirred and held for 30 mins. The pH of the upper aqueous layer was ≦2. The layers were separated, and the lower organic layers washed with brine (450 ml), saturated sodium bicarbonate (500 mL) until pH ≧8. The organic layer was washed with water (450 ml) until pH 6–7 was obtained. The solution was concentrated, acetone (250 ml) added and concentrated. This was repeated with another portion of acetone (250 ml) and concentrated.

The solution was diluted with acetone. 0.5 N Sulfuric acid (500 ml) was added dropwise over 30 mins keeping the pot temperature 0–5° C. The mixture was held for a minimum of 5 h, during which time, the product precipitated out of solution. Aqueous sodium bicarbonate (30 g in 375 ml water) was added dropwise over 30 minutes keeping the pot temperature 0 to 5° C.; the mixture was held for a minimum of 30 minutes. Acetic acid (25 ml) was added until pH was 5–6 keeping the pot temperature <10° C. The mixture was warmed to room temperature and held for 16 h. The solid product was filtered and washed with water (2×100 ml) followed by 1:1 acetone:water (2×100 ml). The cake was purified in acetone (375 ml) to give 65 g (58% overall from rapamycin) of product [B]. LC/MS: using an electrospray interface in the positive ion mode afforded the molecular ion [M+Na]=1138.5 atomic mass units (amu).

Preparation of Rapamycin 42-ester with 2,2-bis(hydroxymethyl)-propionic acid, [C]

Compound [B] (200 g, 0.179 mole), was dissolved in tetrahydrofuran (600 ml), 2-methyl-2,4-pentanediol (42.3 g, 0.358 mole, 2.0 eq.) was added and the mixture stirred for a minimum of 3 h. The reaction mixture was concentrated to a foam. Diethyl ether (1.0 L) was added and the mixture stirred for 2 h. Heptanes (1.0 L) was added dropwise over 1 h and the mixture stirred for 2 h. The mixture was filtered and the solid product washed with heptanes (500 ml). The solids were re-dissolved in acetone (400 ml), re-treated with 2-methyl-2,4-pentanediol (21.1 g, 0.179 mole, 1 eq.) in acetone (200 ml), clarified through a 0.2 micron cartridge filter, and rinsed with acetone (200 ml). The solution was concentrated to a foam, diethyl ether (1.0 L), pre-filtered through a 0.2 micron cartridge filter, was added and the mixture stirred for 2 h. The mixture was co-precipitated by adding pre-filtered heptanes (1.0 L). The precipitated solids were filtered and washed with ether:heptane (2×500 ml). The solids were dried (55 to 60° C., 10 mm Hg, minimum 24 h) to give 159 g (86%) of product [C]. LC/MS: using APCI in the positive ion mode afforded the molecular ion [M+NH$_4$]=1047.0 amu. The $^1$H NMR of the product (CCl-779) was identical to the product described in example 11 of U.S. Pat. No. 5,362,718 (1994).

All patents, patent applications, articles, and other documents referenced herein are incorporated by reference. It will be clear to one of skill in the art that modifications can be made to the specific embodiments described herein without departing from the scope of the invention.

The invention claimed is:

1. A process for preparing a 42-ester of rapamycin, which comprises:
   (a) acylating a rapamycin 31-silyl ether with a compound of formula

HOOC.CR$^7$R$^8$R$^9$ or a mixed 2,4,6-trichlorobenzoyl anhydride thereof, wherein:
   R$^7$ is hydrogen, alkyl of 1–6 carbon atoms, alkenyl of 2–7 carbon atoms, alkynyl of 2–7 carbon atoms, —(CR$^{12}$R$^{13}$)$_f$OR$^{10}$, —CF$_3$, —F, or —CO$_2$R$^{10}$;
   R$^{10}$ is hydrogen, alkyl of 1–6 carbon atoms, alkenyl of 2–7 carbon atoms, alkynyl of 2–7 carbon atoms, triphenylmethyl, benzyl, alkoxymethyl of 2–7 carbon atoms, chloroethyl, or tetrahydropyranyl;
   R$^8$ and R$^9$ are taken together to form X;
   X is a 2-phenyl-1,3,2-dioxaborinan-5-yl or a 2-phenyl-1,3,2-dioxaborinan-4-yl, wherein the phenyl may be optionally substituted;
   R$^{12}$ and R$^{13}$ are each, independently, hydrogen, alkyl of 1–6 carbon atoms, alkenyl of 2–7 carbon atoms, alkynyl of 2–7 carbon atoms, trifluoromethyl, or —F; and
   f=0–6;
   to give a 42-ester boronate 31-silyl ether of rapamycin;
   (b) selectively hydrolyzing the 42-ester boronate 31-silyl ether in mild acidic conditions to provide a rapamycin 42-ester boronate; and
   (c) treating the rapamycin 42-ester boronate with a suitable diol to provide a 42-ester of rapamycin.

2. The process according to claim 1, wherein the 42-ester of rapamycin prepared is CCI-779, and wherein said acylating step (a) comprises acylating rapamycin 31-silyl ether with 5-methyl-2-phenyl-1,3,2-dioxaborinane-5-carboxylic acid or a 2,4,6-trichlorobenzoyl anhydride of 5-methyl-2-phenyl-1,3,2-dioxaborinane-5-carboxylic acid to give rapamycin 31-O-silyl ether, 42-ester boronate.

3. The process according to claim 1, wherein the 31-silyl ether has the formula

—OSiR'R''R''' wherein R', R'' and R''' are the same or different and are selected from the group consisting of alkyl of 1–6 carbon atoms, phenyl and benzyl.

4. The process according to claim 1, wherein the 31-silyl ether is a trimethylsilyl ether.

5. The process according to claim 1, wherein the acylation step (a) is performed with 5-methyl-2-phenyl-1,3,2-dioxaborinane-5-carboxylic acid.

6. The process according to claim 1, in which the acylation step (a) is carried out at less than about 20° C.

7. The process according to claim 6 which is carried out at a temperature of from about –50° C. to about 20° C.

8. The process according to claim 1 in which step (a) is carried out in a solvent comprising methylene chloride.

9. The process according to claim 1 wherein the acid in step (b) is a dilute inorganic acid.

10. The process according to claim 9 wherein the acid is sulphuric, hydrochloric or phosphoric acid.

11. The process according to claim 10, wherein the acid used in step (b) is sulfuric acid.

12. The process according to claim 9, wherein the acid used in step (b) is from about 0.1N to about 3N.

13. The process according to claim 12 wherein the acid used in step (b) is from about 0.2N to about 2N.

14. The process according to claim 12 wherein the acid used in step (b) is about 0.5N.

15. The process according to claim 1 wherein step (b) is carried out in a single phase aqueous acid/organic solvent system.

16. The process according to claim 15 wherein the organic solvent is acetone.

17. The process according to claim 1 wherein step (b) is carried out at a temperature from about 25° C. or below.

18. The process according to claim 17, wherein step (b) is carried out at a temperature from about –5° C. to about 10° C.

19. The process according to claim 17, wherein step (b) is carried out at a temperature from about 0° C. to about 5° C.

20. The process according to claim 1, wherein the diol is a 1,2-, 1,3-, 1,4-, or 1,5-diol.

21. The process according to claim 20, wherein the diol is 2-methyl-2,4-pentane diol.

22. The process according to claim 1 wherein the diol in step (c) is used in an amount of from about 1 to about 5 mole equivalents.

23. The process according to claim 1, in which step (c) is carried out at a temperature of from about –5° C. to about +25° C.

24. The process according to claim 1, in which step (c) carried out in the presence of tetrahydrofuran solvent.

25. The process according to claim 1, which is carried out in the presence of ether solvent.

26. The process according to claim 1 in which the rapamycin 31-O-trimethylsilyl ether, 42-ester boronate has formula:

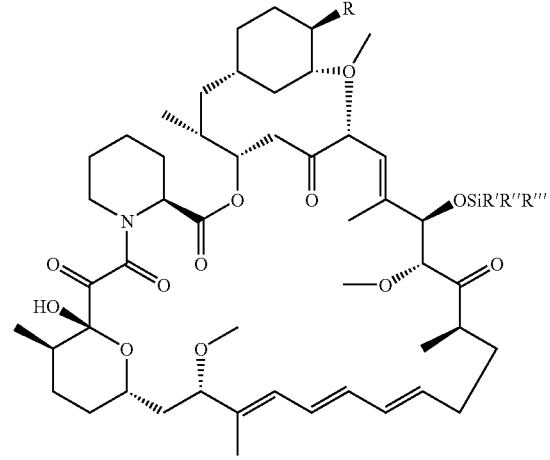

wherein R is —O—C=O.CR$^7$R$^8$R$^9$, wherein:
R$^7$ is hydrogen, alkyl of 1–6 carbon atoms, alkenyl of 2–7 carbon atoms, alkynyl of 2–7 carbon atoms, —(CR$^{12}$R$^{13}$)$_f$OR$^{10}$, —CF$_3$, —F, or —CO$_2$R$^{10}$;
R$^{10}$ is hydrogen, alkyl of 1–6 carbon atoms, alkenyl of 2–7 carbon atoms, alkynyl of 2–7 carbon atoms, triphenylmethyl, benzyl, alkoxymethyl of 2–7 carbon atoms, chloroethyl, or tetrahydropyranyl;
R$^8$ and R$^9$ are taken together to form X;
X is 2-phenyl-1,3,2-dioxaborinan-5-yl or 2-phenyl-1,3,2-dioxaborinan-4-yl,
wherein the phenyl may be optionally substituted;
R$^{12}$ and R$^{13}$ are each, independently, hydrogen, alkyl of 1–6 carbon atoms, alkenyl of 2–7 carbon atoms, alkynyl of 2–7 carbon atoms, trifluoromethyl, or —F;

and
f=0–6.

27. The process according to claim 1 in which the rapamycin 42-boronate ester has the formula:

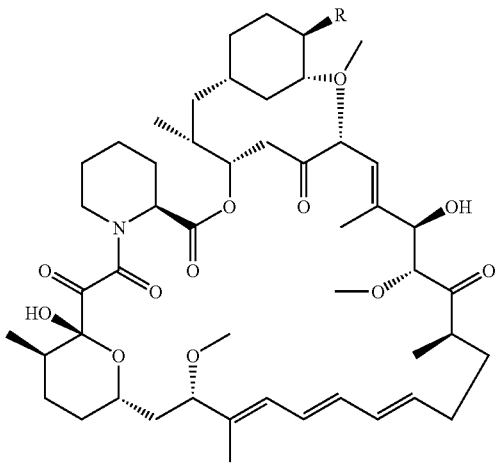

wherein R is —O—C═O.CR$^7$R$^8$R$^9$, wherein:

R$^7$ is hydrogen, alkyl of 1–6 carbon atoms, alkenyl of 2–7 carbon atoms, alkynyl of 2–7 carbon atoms, —(CR$^{12}$R$^{13}$)$_f$ OR$^{10}$, —CF$_3$, —F, or —CO$_2$R$^{10}$;

R$^{10}$ is hydrogen, alkyl of 1–6 carbon atoms, alkenyl of 2–7 carbon atoms, alkynyl of 2–7 carbon atoms, triphenylmethyl, benzyl, alkoxymethyl of 2–7 carbon atoms, chloroethyl, or tetrahydropyranyl;

R$^8$ and R$^9$ are taken together to form X;

X is 2-phenyl-1,3,2-dioxaborinan-5-yl or 2-phenyl-1,3,2-dioxaborinan4-yl, wherein the phenyl may be optionally substituted;

R$^{12}$ and R$^{13}$ are each, independently, hydrogen, alkyl of 1–6 carbon atoms, alkenyl of 2–7 carbon atoms, alkynyl of 2–7 carbon atoms, trifluoromethyl, or —F;

and
f=0–6.

28. A process for preparing a compound of formula:

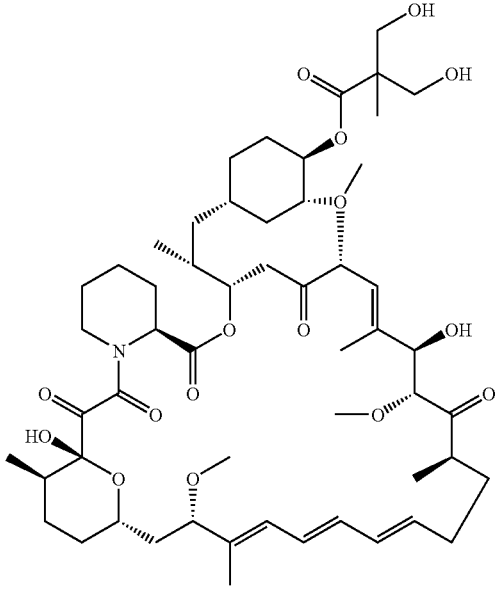

which comprises treating a 31-silyl ether, rapamycin 42-boronate ester with an alkyl substituted diol.

29. The process according to claim 28 wherein the diol used is a 1,2-, 1,3-, 1,4-, or 1,5-diol.

30. The process according to claim 28 wherein the diol is 2-methyl-2,4-pentane diol.

31. The process according to claim 28 wherein the diol is used in an amount of from about 1 to about 5 mole equivalents.

32. The process according to claim 28, which is carried out at a temperature of from about −5° C. to about +25° C.

33. The process according to claim 28, which is carried out in the presence of tetrahydrofuran solvent.

34. The process according to claim 28, which is carried out in the presence of ether solvent.

35. A process for preparing 5-methyl-2-phenyl-1,3,2-dioxaborinane-5-carboxylic acid, which comprises:

reacting 2,2-bis(hydroxymethyl)propionic acid with phenylboronic acid.

36. The process as claimed in 35, which is carried out in the presence of tetrahydrofuran solvent.

37. A process for increasing the purity of a compound of formula

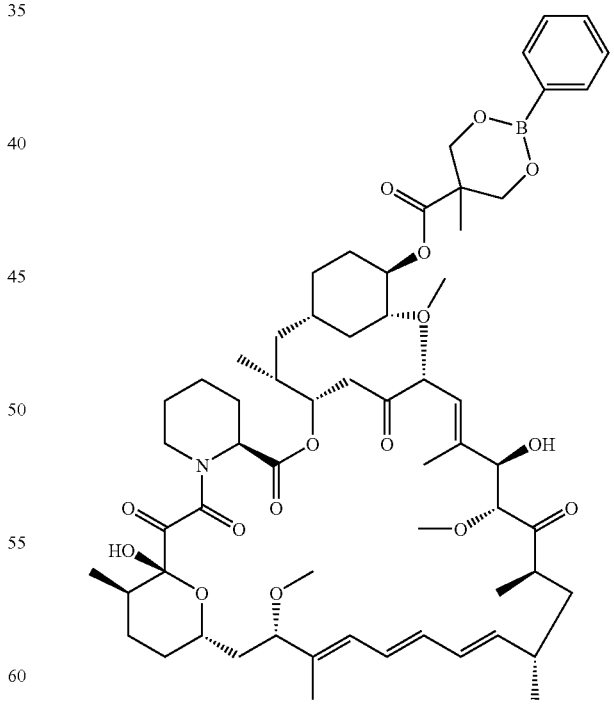

in a solution containing isomers B and C in a ratio of <about 10:1

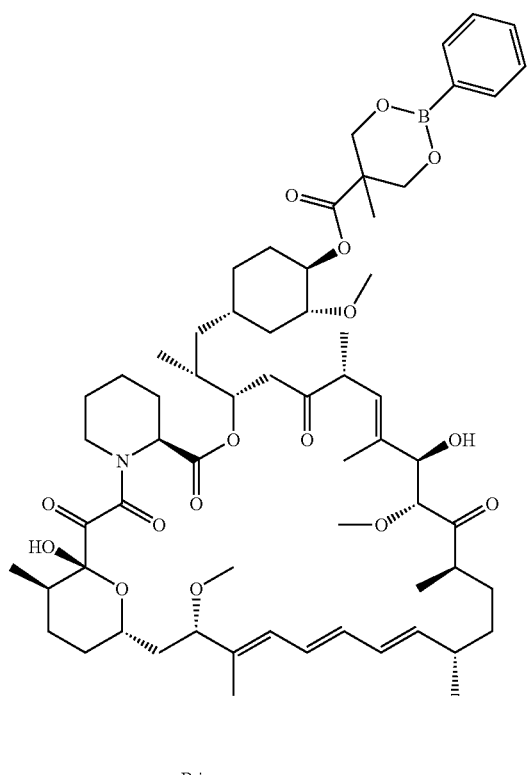

B isomer and

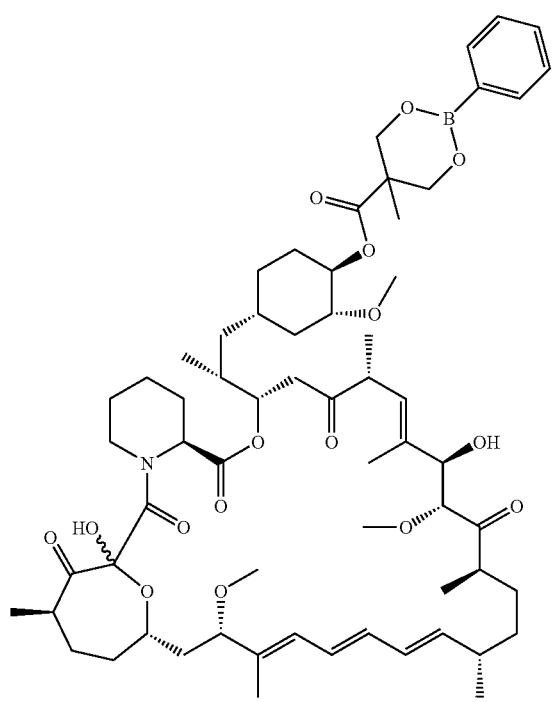

C isomer comprising the step of adjusting the pH of the solution to a pH of about 5 to about 6.

38. The process according to claim 37, which is carried out in the presence of acetone solvent.

39. The process according to claim 37, which is carried out in the presence of sodium acetate buffer.

40. The process according to claim 37, which is carried out in the presence of sodium bicarbonate and acetic acid.

41. A compound of formula (I):

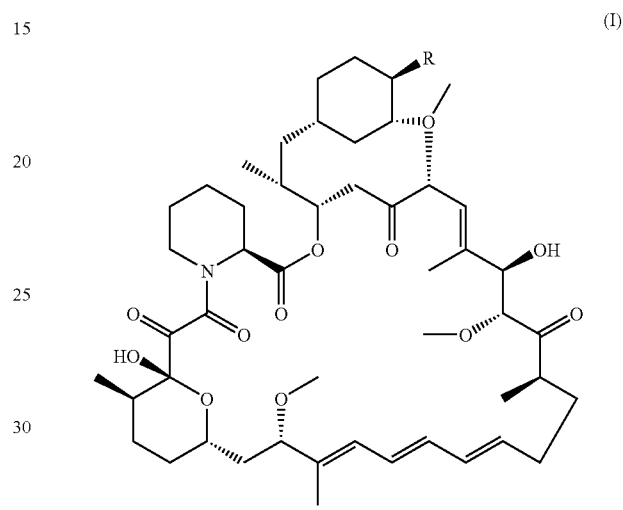

(I)

in which R is:

wherein:

$R^7$ is hydrogen, alkyl of 1–6 carbon atoms, alkenyl of 2–7 carbon atoms, alkynyl of 2–7 carbon atoms, —$(CR^{12}R^{13})_f$—$OR^{10}$, —$CF_3$, —F, or —$CO_2R^{10}$;

$R^{10}$ is hydrogen, alkyl of 1–6 carbon atoms, alkenyl of 2–7 carbon atoms, alkynyl of 2–7 carbon atoms, triphenylmethyl, benzyl, alkoxymethyl of 2–7 carbon atoms, chloroethyl, or tetrahydropyranyl;

$R^8$ and $R^9$ are taken together to form X;

X is 2-phenyl-1,3,2-dioxaborinan-5-yl or 2-phenyl-1,3,2-dioxaborinan-4-yl, wherein the phenyl may be optionally substituted;

$R^{12}$ and $R^{13}$ are each, independently, hydrogen, alkyl of 1–6 carbon atoms, alkenyl of 2–7 carbon atoms, alkynyl of 2–7 carbon atoms, trifluoromethyl, or —F;

and f=0–6.

42. A compound of formula:

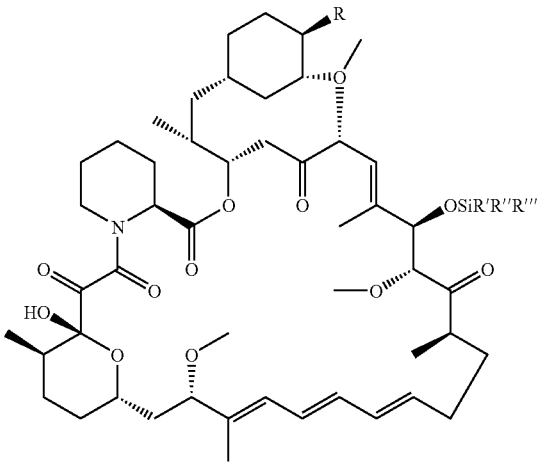

in which R is:

—O—C=O.CR⁷R⁸R⁹ wherein:
R⁷ is hydrogen, alkyl of 1–6 carbon atoms, alkenyl of 2–7 carbon atoms, alkynyl of 2–7 carbon atoms, —(CR¹²R¹³)$_f$OR¹⁰, —CF₃, —F, or —CO₂R¹⁰;
R¹⁰ is hydrogen, alkyl of 1–6 carbon atoms, alkenyl of 2–7 carbon atoms, alkynyl of 2–7 carbon atoms, triphenylmethyl, benzyl, alkoxymethyl of 2–7 carbon atoms, chloroethyl, or tetrahydropyranyl;
R⁸ and R⁹ are taken together to form X;
X is 2-phenyl-1,3,2-dioxaborinan-5-yl or 2-phenyl-1,3,2-dioxaborinan-4-yl,
wherein the phenyl may be optionally substituted;
R¹² and R¹³ are each, independently, hydrogen, alkyl of 1–6 carbon atoms, alkenyl of 2–7 carbon atoms, alkynyl of 2–7 carbon atoms, trifluoromethyl, or —F;
and
f=0–6;
and wherein R', R", and R'" are the same or different and are selected from the group consisting of alkyl of 1–6 carbon atoms, phenyl and benzyl.

43. A compound which is rapamycin 42-ester with 5-methyl-2-phenyl-1,3,2-dioxaborinane-5-carboxylic acid.

44. A compound in which is rapamycin 31-O-trimethylsilyl ether, 42-ester with 5-methyl-2-phenyl-1,3,2-dioxaborinane-5-carboxylic acid.

45. A compound of formula:

HO—C=O.CR⁷R⁸R⁹

R⁷ is hydrogen, alkyl of 1–6 carbon atoms, alkenyl of 2–7 carbon atoms, alkynyl of 2–7 carbon atoms, —(CR¹²R¹³)$_f$OR¹⁰, —CF₃, —F, or —CO₂R¹⁰;

R¹⁰ is hydrogen, alkyl of 1–6 carbon atoms, alkenyl of 2–7 carbon atoms, alkynyl of 2–7 carbon atoms, triphenylmethyl, benzyl, alkoxymethyl of 2–7 carbon atoms, chloroethyl, or tetrahydropyranyl;
R⁸ and R⁹ are taken together to form X;
X is a 2-phenyl-1,3,2-dioxaborinan-5-yl or a 2-phenyl-1,3,2-dioxaborinan-4-yl, wherein the phenyl may be optionally substituted;
R¹² and R¹³ are each, independently, hydrogen, alkyl of 1–6 carbon atoms, alkenyl of 2–7 carbon atoms, alkynyl of 2–7 carbon atoms, trifluoromethyl, or —F;
and
f=0–6;
or a mixed 2,4,6-trichlorobenzoyl anhydride thereof.

46. The compound according to claim 45 which is 5-methyl-2-phenyl-1,3,2-dioxaborinane-5-carboxylic acid, wherein the phenyl is optionally substituted; or a 2,4,6-trichlorobenzoyl mixed anhydride thereof.

47. The compound according to claim 45 which is 5-methyl-2-phenyl-1,3,2-dioxaborinane-5-carboxylic acid or a 2,4,6-trichlorobenzoyl mixed anhydride thereof.

48. A process for preparing a 42-ester of rapamycin, which comprises:
(b) acylating a rapamycin 31-silyl ether with a compound of formula

HOOC.CR⁷R⁸R⁹ or a mixed 2,4,6-trichlorobenzoyl anhydride thereof, wherein
R⁷ is hydrogen, alkyl of 1–6 carbon atoms, alkenyl of 2–7 carbon atoms, alkynyl of 2–7 carbon atoms, —(CR¹²R¹³)$_f$OR¹⁰, —CF₃, —F, or —CO₂R¹⁰;
R¹⁰ is hydrogen, alkyl of 1–6 carbon atoms, alkenyl of 2–7 carbon atoms, alkynyl of 2–7 carbon atoms, triphenylmethyl, benzyl, alkoxymethyl of 2–7 carbon atoms, chloroethyl, or tetrahydropyranyl;
R⁸ and R⁹ are taken together to form X;
X is a 2-phenyl-1,3,2-dioxaborinan-5-yl or a 2-phenyl-1,3,2-dioxaborinan-4-yl, wherein the phenyl may be optionally substituted;
R¹² and R¹³ are each, independently, hydrogen, alkyl of 1–6 carbon atoms, alkenyl of 2–7 carbon atoms, alkynyl of 2–7 carbon atoms, trifluoromethyl, or —F; and
f=0–6;
to give a 42-ester boronate 31-silyl ether of rapamycin;
(b) selectively hydrolyzing the 42-ester boronate 31-silyl ether in mild acidic conditions to provide a rapamycin 42-ester boronate; and
(c) treating the rapamycin 42-ester boronate with diethanolamine, solid-supported polystyrene diethanolamine, or a carboxylic acid to provide a 42-ester of rapamycin.

49. The process according to claim 48, wherein said carboxylic acid is oxalic, malonic tartaric, phthalic acid, or salicylic acid.

* * * * *

UNITED STATES PATENT AND TRADEMARK OFFICE
CERTIFICATE OF CORRECTION

PATENT NO. : 7,153,957 B2
APPLICATION NO. : 10/903062
DATED : December 26, 2006
INVENTOR(S) : Warren Chew and Chia-Cheng Shaw It is certified that error appears in the above-identified patent and that said Letters Patent is hereby corrected as shown below:

Col. 6, replace the following structure spanning lines 38-65:

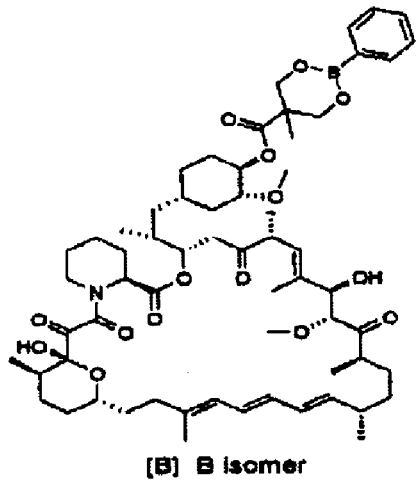

with the following structure:

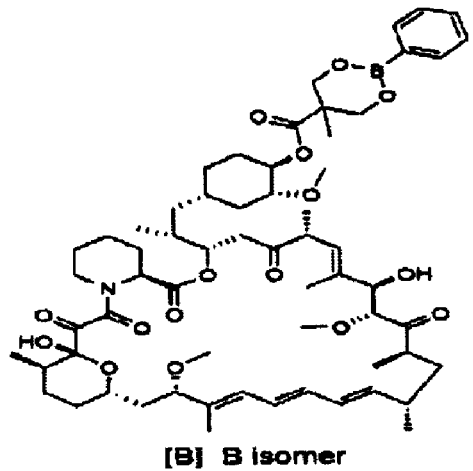

UNITED STATES PATENT AND TRADEMARK OFFICE
CERTIFICATE OF CORRECTION

PATENT NO.         : 7,153,957 B2
APPLICATION NO.    : 10/903062
DATED              : December 26, 2006
INVENTOR(S)        : Warren Chew and Chia-Cheng Shaw It is certified that error appears in the above-identified patent and that said Letters Patent is hereby corrected as shown below:

Col. 7, replace the following structure spanning lines 1-30:

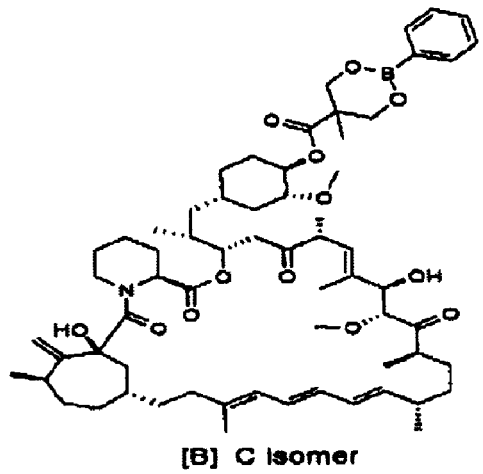

with the following structure:

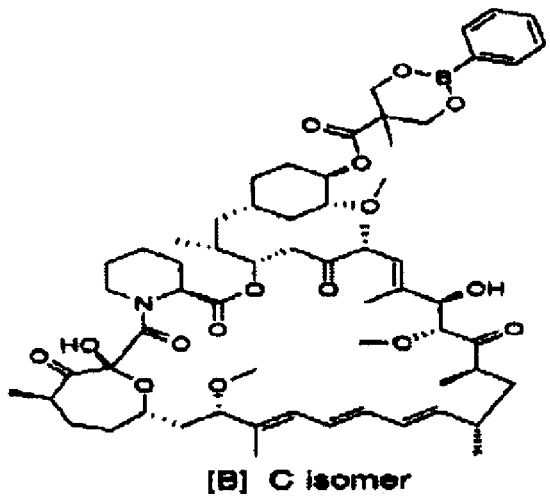

UNITED STATES PATENT AND TRADEMARK OFFICE
CERTIFICATE OF CORRECTION

PATENT NO. : 7,153,957 B2  Page 3 of 4
APPLICATION NO. : 10/903062
DATED : December 26, 2006
INVENTOR(S) : Warren Chew and Chia-Cheng Shaw It is certified that error appears in the above-identified patent and that said Letters Patent is hereby corrected as shown below:

Replace the scheme spanning cols. 7-12, with the following scheme:

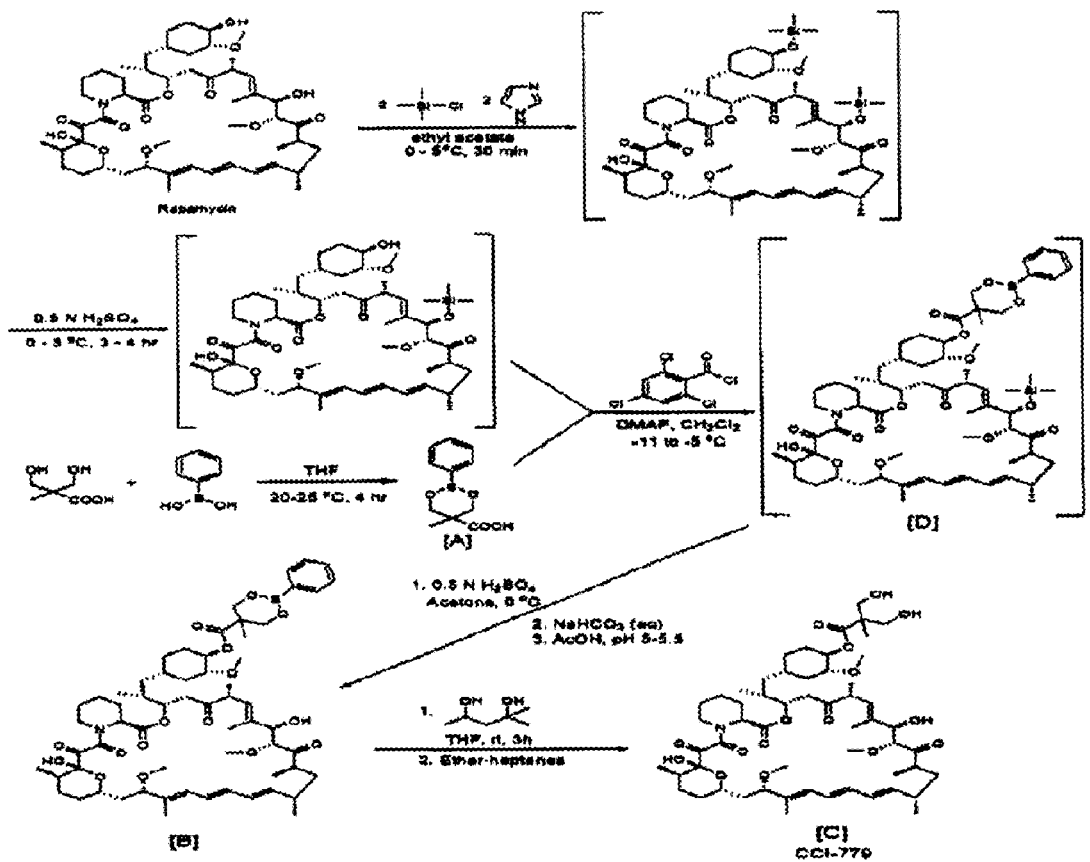

UNITED STATES PATENT AND TRADEMARK OFFICE
CERTIFICATE OF CORRECTION

PATENT NO. : 7,153,957 B2
APPLICATION NO. : 10/903062
DATED : December 26, 2006
INVENTOR(S) : Warren Chew and Chia-Cheng Shaw It is certified that error appears in the above-identified patent and that said Letters Patent is hereby corrected as shown below:

Col. 16, Claim 24, add -- is -- after (c)

Col. 17, Claim 27, replace "4-yl," with -- -4-yl, --;

Signed and Sealed this

Fifteenth Day of April, 2008

JON W. DUDAS
*Director of the United States Patent and Trademark Office*